United States Patent [19]
Beier et al.

[11] 4,317,112
[45] Feb. 23, 1982

[54] ARRANGEMENT FOR DETERMINING THE REMOVAL OF WORK TOOLS AND/OR DRIVE ELEMENTS FROM RECEIVING LOCATIONS, PARTICULARLY FOR A DENTAL TREATMENT LOCATION

[75] Inventors: Stefan Beier; Hermann Gmeinder, both of Biberach, Fed. Rep. of Germany

[73] Assignee: Kaltenbach & Voight GmbH & Co., Fed. Rep. of Germany

[21] Appl. No.: 81,400

[22] Filed: Oct. 3, 1979

[30] Foreign Application Priority Data

Oct. 11, 1978 [DE] Fed. Rep. of Germany ....... 2844347

[51] Int. Cl.³ .................... G08B 21/00; G08B 13/26
[52] U.S. Cl. .................................. 340/568; 340/518; 340/679
[58] Field of Search ................. 340/568, 561, 518, 51, 340/679; 307/116; 331/65

[56] References Cited

U.S. PATENT DOCUMENTS

| | | | |
|---|---|---|---|
| 2,474,157 | 6/1949 | Needlman | 340/568 |
| 3,201,774 | 8/1965 | Uemura | 340/568 |
| 3,376,547 | 4/1968 | Auer, Jr. | 340/51 |
| 3,644,927 | 2/1972 | Green | 340/518 |
| 4,042,918 | 8/1977 | Klitzman | 340/568 |
| 4,088,899 | 5/1978 | Miller et al. | 307/116 |

*Primary Examiner*—Glen R. Swann, III
*Attorney, Agent, or Firm*—Scully, Scott, Murphy & Presser

[57] ABSTRACT

An arrangement for a dental treatment facility for detecting the removal of work tools and/or drive elements utilized during the operation of the work tools from receiving locations provided therefor.

4 Claims, 7 Drawing Figures

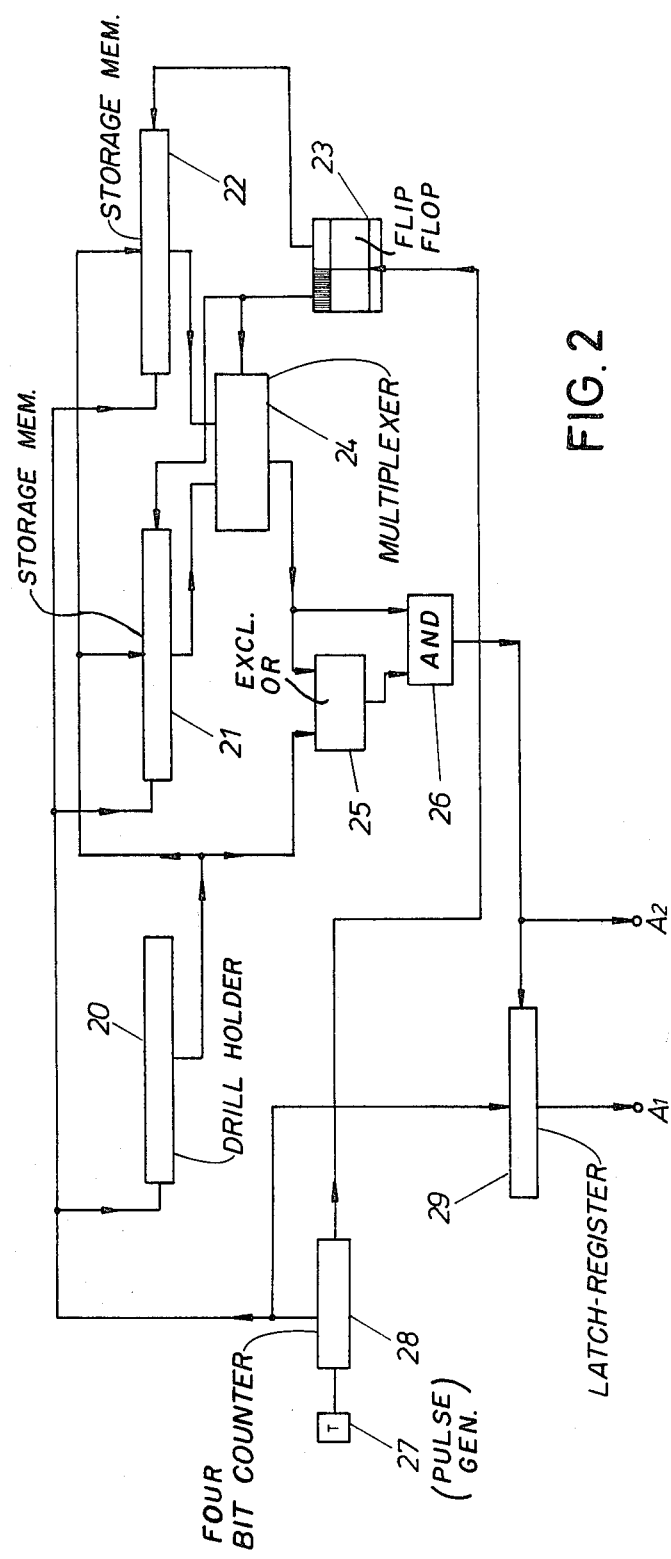

ARRANGEMENT FOR DETERMINING THE REMOVAL OF WORK TOOLS AND/OR DRIVE ELEMENTS FROM RECEIVING LOCATIONS, PARTICULARLY FOR A DENTAL TREATMENT LOCATION

BACKGROUND OF THE INVENTION

1. Field of the Invention

The present invention relates to an arrangement for a dental treatment facility for detecting the removal of work tools and/or drive elements utilized during the operation of work tools from receiving locations provided therefor.

2. Discussion of the Prior Art

The detection of the removal of work tools or various elements from receiving locations provided for the receipt thereof, in principle can be effected in a manner in which mechanical contacts are associated with the individual receiving locations which are either opened or closed upon the removal of the respective element. Thereby, through the intermediary of an interrogating arrangement, the switch condition indicates the presence of or, respectively, the removal of an element of that type. However, this type of arrangement it is disadvantageous in that the contact making is not reliable under all circumstances, which leads to erroneous determinations of the removal of elements or, respectively, work tools from their present receiving location.

SUMMARY OF THE INVENTION

Accordingly, it is an object of the present invention to provide an arrangement through the intermediary of which it is possible to achieve a particularly reliable and simple detection of the removal of work tools and/or drive elements utilized during the operation of work tools from the receiving locations provided for their receipt or storage.

The foregoing object is inventively achieved in that, in a detection arrangement of the above-mentioned type, a coil is associated with each receiving location, and is connected with an oscillation generator the oscillation signals of which possess different values in their amplitude at the presence or, respectively, absence of a work tool, or respectively, drive element at the associated receiving location. A change in amplitude from a reference value is utilized for the delivery of an indicating signal.

The foregoing invention has the advantage of providing in a relatively simple manner, the detection of the removal of work tools and/or drive elements utilized during the operation of these work tools from their receiving locations without the difficulties encountered with the opening or, respectively, closing of contacts. Moreover, the invention provides for the further advantage that it relies upon the formation of an eddy current in the present workpiece or, respectively, drive element as a plottable value. Accordingly practically no limitations are present with regard to the material which is to be employed for the work tools or drive elements.

Suitably, the coils of the collective receiving locations are cyclically connected in sequence with the oscillator generator. This affords a particularly simple technical construction with regard to the circuitry.

The indicating signals corresponding to the oscillating signals during two successive interrogation cycles of the same receiving location are suitably stored in two separate memory storages, and the indicating signals of the two stored signals for the same receiving location are compared with each other with the delivery of an indicating signal. This results in the advantage of a particularly low technological demand on the circuitry for effectuation of the so-called last-look principle.

Preferably the invention provides for an address generator which delivers addresses designating the collective receiving or storage locations. From the address signals, control signals can be tapped off by means of a decoder for closing of switches through which the coils are connected with the oscillation generator. Hereby, there is thus obtained the advantage of a particularly simple technical construction with regard to the circuitry employed for the connection of the individual coils with the single oscillation generator.

After the removal of a work tool, or a drive element from the receiving or storage location associated therewith, an indicator element located at this receiving location is operatively controllable for delivery of an indicating signal, particularly a flashing signal. In this manner, it is assured that the particular receiving location is especially designated at which a currently removed work tool or drive element is to be redeposited after utilization thereof.

BRIEF DESCRIPTION OF THE DRAWINGS

Reference may now be had to the following detailed description of the invention, taken in conjunction with the accompanying drawings; in which:

FIG. 2 illustrates a schematic circuit block diagram of an embodiment of an interrogating device provided in the arrangement of FIG. 1;

DETAILED DESCRIPTION

Figure 1:
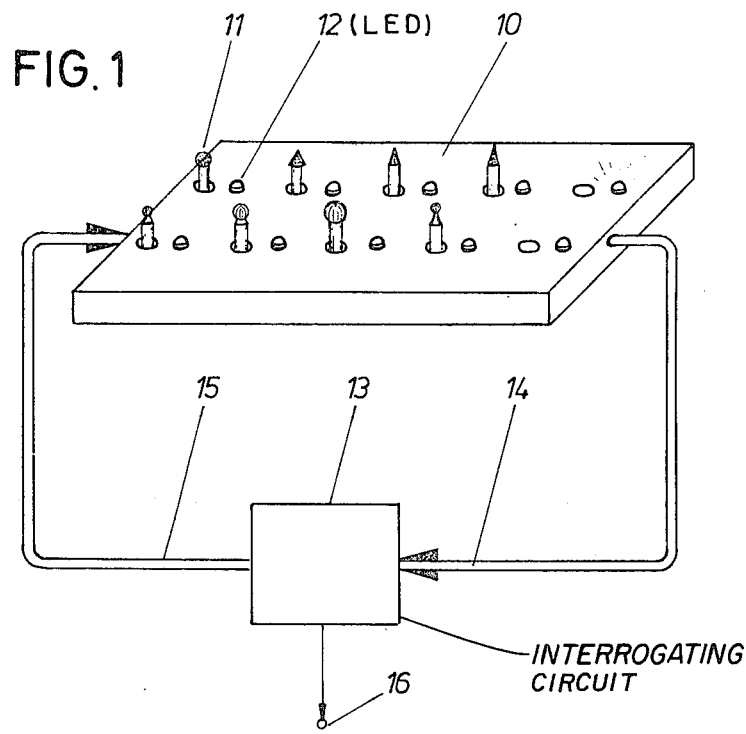
FIG. 1 is a generally schematic perspective view of an arrangement constructed pursuant to the invention.

The arrangement illustrated in FIG. 1 illustrates a work tool receiving or storage arrangement 10 for a dental treatment location. This work tool receiving arrangement 10 is equipped with a plurality of receiving locations for work tools 11, which may relate to dental drills. Each receiving location has an indicator element 12 associated therewith, for example, in the form of a luminescent diode or a light bulb. Connected with the work tool receiving arrangement 10 is an interrogating arrangement 13 through the intermediary of two control cables 14, 15. Through the control cable 14, the interrogating arrangement 13 interrogates the individual receiving locations of the work tool receiving arrangement 10 with regard to the presence or absence of a work tool. By means of the control cable 15, the interrogating arrangement 13 controls the individual indicator elements 12. This can be effected in the manner wherein that particular indicator element 12 is brought into illumination or flashing from whose associated receiving location there has been removed a work tool 11. The removal of a work tool 11 from its receiving or storage location is signaled by the interrogating arrangement 13 through the delivery of a corresponding indicator signal which can be taken off from an output connection 16.

In FIG. 2, on the basis of a circuit block diagram, there is more closely illustrated the interrogating arrangement 13 of FIG. 1, for example, for sixteen work tools. According to FIG. 2, a 4-bit counter 28 which is controlled by a pulse generator 27 delivers sequential addresses for the addressing of two read-record storages 21 and 22, as well as for the addressing of a drill stand or holder 20 corresponding to a work tool receiving arrangement 10 pursuant to FIG. 1. In this drill stand 20, the individual receiving locations for the work tools are controlled correspondingly addressed, whereby the respective result is conducted in the form of a bit to the recording inputs of the two storages 21 and 22 and, moreover, to the one input of an exclusive OR gate 25. This exclusive OR gate 25 has the output thereof connected with the input of an AND gate 26. The other input of this AND gate 26 is connected with the other input of the exclusive OR gate 25 at the output of a multiplexer 24 which, in accordance with its position, connects either the output of the storage 21 or the output of the storage 22 with the just above-mentioned inputs of the two connecting elements 25 and 26. The setting of the multiplexer 24 activates a bistable flip-flop 23 which, moreover, has its two outputs connected with the control inputs of the two storages 21 and 22. In accordance with the control position one of these two storages 21, 22 is presently found to be in a recording operation, whereas the other storage 22 or, respectively, 21 is presently in a reading operation. The storage which is found to be in reading operation has its output then connected through the multiplexer 24 with the mutually interconnected inputs of the two connecting elements 25 and 26.

The bistable flip-flop 23 has a pulsing input connected to a transfer-output of the counter 28. As a result, the bistable flip-flop 23 will then presently switch over when the counter 28 has traversed its collective count positions.

Connected to the output of the AND gate 26 is a 4-bit latch register 29 with a release input. This register 29 represents an acceptance register which at a corresponding control of the AND gate 26 assumes at the appropriate point in time the address delivered from the counter 28. This address then indicates the register 29 as that address at an output connection A1 which designates a receiving location from which a work tool has just been removed. The output of the AND gate 26 is connected with a further output connector A2. At this output connector A2 there will appear a "1"-bit when a work tool has actually been removed from a storage location of the tool receiving or holding arrangement.

Figure 3:
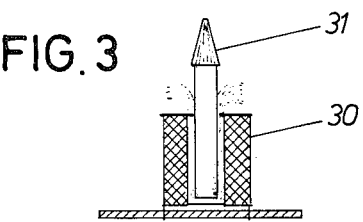
FIG. 3 illustrates schematically, in a sectional view, a possibility for the storage of a work tool in a receiving location.
Figure 4:
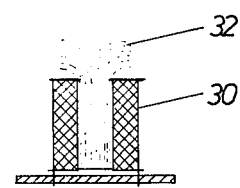
FIG. 4 illustrates the receiving location shown in FIG. 3 without a work tool.

In order to be able to recognize the removal of a work tool from its associated receiving location, a coil 30 is associated with each receiving location, as may be ascertained from FIGS. 3 and 4 of the drawings. Herein, FIG. 3 illustrates the instance in which the coil 30, which is constructed as an air-core solenoid, has a work tool 31 positioned therein. In contrast therewith FIG. 4 shows the instance in which no work tool is positioned within the coil 30. A comparative view of FIGS. 3 and 4 leads to the recognition that in the case of FIG. 4 the coil 30 possesses a more intense leakage field 32.

Figure 5:
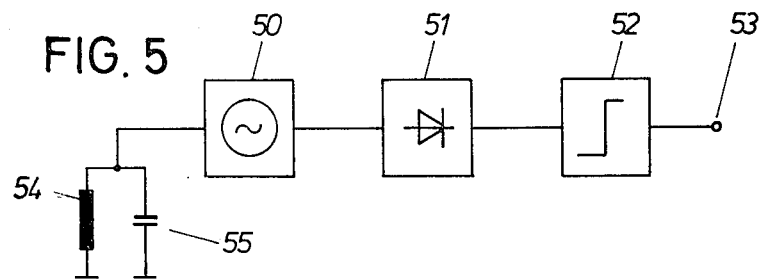
FIG. 5 illustrates a schematic circuit block diagram of a circuit arrangement which can be provided for each work tool receiving location.

Each of the thus provided coils may now be incorporated in an evaluating arrangement in the manner shown in FIG. 5. This evaluating arrangement individually encompasses an oscillation generator or, respectively, oscillator 15 whose oscillation frequency is determined through the inductance of a coil 54 and the capacitance of a condensor 55. The oscillation amplitude of the oscillation generator 50 depends upon a magnitude of the leakage field of the pertinent coil. Connected to the output of the oscillation generator 50 is a rectifier circuit 51 which is connected to the input of an amplitude threshold circuit 52, for example, a comparator, which is adapted to deliver output signals at an output 53.

Figure 6:
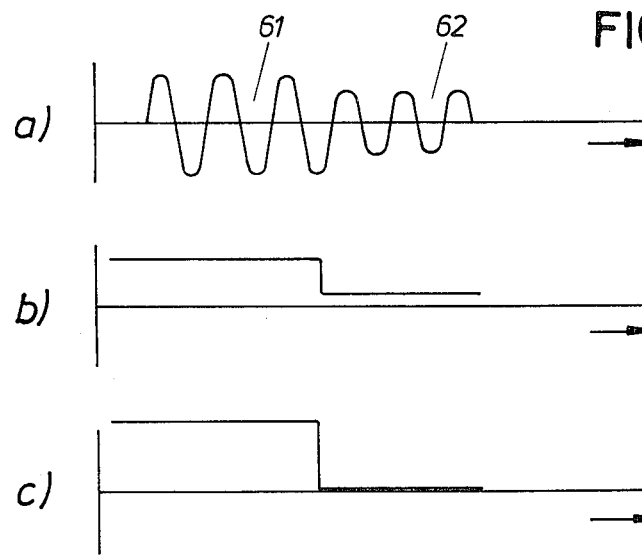
FIG. 6 illustrates a single-time graph showing the sequence of signals at different points in the circuit arrangement represented in FIG. 5.

In order to render more explicit the mode of operation of the circuit arrangement illustrated in FIG. 5, reference is now had to FIG. 6 of the drawings. In FIG. 6a there is illustrated the sequence of the oscillation signals emitted by the oscillation generator 50 pursuant to FIG. 5. Hereby, through the signal sequence 61 there is indicated that a work tool, such as the work tool 31, has been removed from its associated coil 30. The signal sequence 62 illustrates the oscillation amplitude of the oscillation generator 50 for the instance in which a work tool, such as the work tool 31, is arranged within its associated coil 30. From these oscillation signals 61, 62 which are indicated in FIG. 6a, the rectifier circuit 51 generates the signal represented in FIG. 6b, which then leads to the output of the signal illustrated in FIG. 6c from the output 53 of the circuit arrangement according to FIG. 5. From the foregoing it should be ascertainable that it is possible to obtain a singular determination of the presence or absence of a work tool at its associated receiving location.

Figure 7:
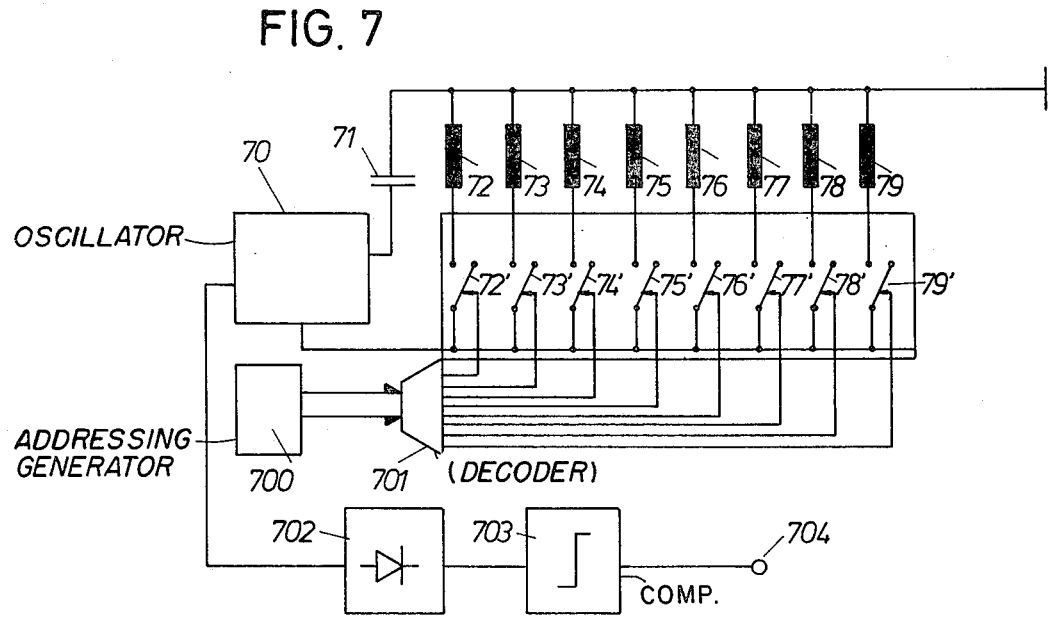
FIG. 7 illustrates a schematic circuit block diagram of a circuit arrangement which can be provided for a plurality of work tool receiving locations.

Illustrated in FIG. 7 of the drawings is a modification of the circuitry principle represented in FIG. 5. Pursuant to FIG. 7, the coils 72 through 79 which are associated with the individual receiving locations are not presently connected with their own oscillation generator but, in contrast therewith, are associated with a single oscillation generator or, respectively, oscillator 7. Hereby, the oscillation frequency of the oscillation generator 70, as in the circuit arrangement illustrated in FIG. 5, is determined through the capacitance of a condensor 71 and through the inductance of the currently utilized coil of the coils 72 through 79. These coils 72 through 79 have one of their ends commonly connected with one side of the condensor 71 to ground. These coils 72 through 79 have their other ends connected to their individually associated switches 72' through 79', through which the single coils 72 through 79 can be individually connected with the oscillator 70. In order to produce these connections, the actuating inputs of the above-mentioned switches 72' through 79' have conducted thereto corresponding actuating signals from the output of a decoder 701. The decoder 701 is connected through an addressing conduit to the output of an addressing generator 700. This addressing generator 700 may cyclically sequentially deliver such addresses so that sequentially each of the switches 72' through 79' is closed for a short interval. During the closing interval of the respective switch, the coil which is connected with the switch, such as the coil 72, is drawn into the oscillation circuit of the oscillation generator or, respectively, oscillator 70. As in the circuit arrangement illustrated in FIG. 5, also in the circuit arrangement pursuant to FIG. 7 does the output of the oscillator 70 have a rectifier circuit 702 connected thereto which, in turn, has an evaluating circuit, such as a comparator 703, connected to the output thereof. This evaluating circuit 703 delivers corresponding output signals at an output 704. In principle, the circuit arrangement illustrated in FIG. 7 operates as that elucidated with regard to FIG. 6.

Finally, it is also to be indicated that the present invention is explained preferably with reference to a work tool receiving arrangement and with reference to the removal of work tools from the associated receiving or holding locations out of the pertinent work tool receiving arrangement. However, mention must be made that the present invention may, in principle be employed in the same manner also for the determination of the removal of drive elements or other elements which, occasionally, can be utilized in conjunction with the respective work tools. Such an instance in use is present particularly in a dental treatment location. Hereby, it is usual to so proceed that for each group of elements, such as work tools and drive elements, the previously explained arrangements have specially provided arrangements.

In connection with the circuit arrangement illustrated in FIG. 2, there can finally be also remarked that the last-look principle inherent to this circuit arrangement is brought therewith whereby the collective receiving locations of the current receiving arrangement need not be occupied, in order to deliver a valid indication at the removal of an element from its associated receiving location.

What is claimed is:

1. In an arrangement for detecting the removal of work tools or of drive elements utilized for driving work tools from receiving locations provided for the storage thereof in a dental treatment facility, and for delivering signals indicative of their removal, the improvement comprising: a coil associated with each receiving location, an oscillation generator connected with said coils and delivering oscillation signals, the amplitudes of which are indicative of the presence or absence of a work tool or drive element from its associated receiving location, and means for detecting the occurrence of a change in amplitude from a reference value to produce the indicator signal.

2. Arrangement as claimed in claim 1, including means for cyclically connecting in sequence the coils of said receiving locations with said oscillation generator.

3. Arrangement as claimed in claim 2, including two separate memory storages, means for storing the oscillation signals produced on the addressing of a single receiving location during two sequential addressing cycles in said two separate memory storages, and means for comparing the signals in said two memory storages.

4. Arrangement as claimed in claim 3, including an addressing generator for delivering addresses designating the receiving locations, a decoder, and switch means, said decoder tapping off control signals from said addresses for closing said switch means to connect said coils to said oscillation generator.

* * * * *